(12) United States Patent
Silva et al.

(10) Patent No.: US 12,364,804 B1
(45) Date of Patent: Jul. 22, 2025

(54) PORTABLE DOUCHING APPARATUS

(71) Applicant: SQUWASH LLC, Kaneohe, HI (US)

(72) Inventors: Colin M. K. Silva, San Francisco, CA (US); Justin Aiello, Kennebunk, ME (US); Marvin V. Silva, Gig Harbor, WA (US)

(73) Assignee: SQUWASH LLC, Kaneohe, HI (US)

( * ) Notice: Subject to any disclaimer, the term of this patent is extended or adjusted under 35 U.S.C. 154(b) by 0 days.

(21) Appl. No.: 18/958,857

(22) Filed: Nov. 25, 2024

Related U.S. Application Data

(60) Provisional application No. 63/686,171, filed on Aug. 23, 2024.

(51) Int. Cl.
*A61M 3/02* (2006.01)
*A61M 39/12* (2006.01)

(52) U.S. Cl.
CPC .......... *A61M 3/0216* (2014.02); *A61M 3/022* (2014.02); *A61M 3/0233* (2013.01); *A61M 39/12* (2013.01); *A61M 2205/0216* (2013.01)

(58) Field of Classification Search
CPC .... A61M 3/02; A61M 3/0204; A61M 3/0216; A61M 3/022; A61M 3/0233; A61M 3/025; A61M 3/0279; A61M 39/12; A61M 39/22; A61M 2205/0216; B05B 1/18; B05B 1/00; A01K 13/001; A61D 7/00; A61D 11/00
See application file for complete search history.

(56) References Cited

U.S. PATENT DOCUMENTS 6,589,216 B1 * 7/2003 Abbott ................ A61M 3/0216
                                                    604/257
10,393,300 B1    8/2019 Lane
(Continued)

FOREIGN PATENT DOCUMENTS

WO    WO-2023193863 A1 * 10/2023 .......... A61M 3/0216

OTHER PUBLICATIONS

Cleanstream Shower Enema System, 6-Foot Hose, 5-Inch and 3.5-Inch Nozzles, Water Flow Regulator, Rubber Washers, Cleaner Kit for Men and Women, https://www.amazon.com/Cleanstream-3-5-Inch-Nozzles-Regulator-Washers/dp/B002FCN7Y2 (product first available Nov. 10, 2008).

(Continued)

*Primary Examiner* — Kami A Bosworth
*Assistant Examiner* — Avery Smale
(74) *Attorney, Agent, or Firm* — Leonid Kisselev

(57) ABSTRACT

A portable douching apparatus that provides efficient and safe internal cleansing is disclosed. The douching apparatus can be used in the shower, offering a portable, discreet, and efficient, shower-powered solution for douching without the need for tools or installation. As described below, the apparatus includes a self-sealing elastomeric connector that allows a secure mounting on a shower or another water-providing fixture, a water pressure release mechanism that allows to reduce internal water pressure that could disrupt the connection to the fixture, and body-safe tip optimized for insertion into an orifice of a living organism. These features ensure a hygienic, safe internal use and compatibility with a narrow-diameter hose and tip, allowing the device to function under various levels of shower water pressure and providing a significant improvement over existing douching products.

16 Claims, 9 Drawing Sheets

(56) References Cited

U.S. PATENT DOCUMENTS

| | | | |
|---|---|---|---|
| 11,085,567 B2 | 8/2021 | Lane | |
| 11,365,838 B1 | 6/2022 | Lane | |
| 11,774,021 B1 | 10/2023 | Lane | |
| 11,913,577 B2 | 2/2024 | Lane | |
| 2022/0031519 A1* | 2/2022 | Hardman | A61M 1/96 |
| 2022/0226560 A1* | 7/2022 | Gonzales | A61M 3/0241 |
| 2023/0364626 A1* | 11/2023 | Kajuch | B05B 1/185 |
| 2024/0261494 A1* | 8/2024 | Okpala-Ezechukwu | A61M 3/0279 |

OTHER PUBLICATIONS

Cleanstream Aqua Shot Deep Shower EnemaDouche Cleansing System, Black, https://www.amazon.com/Cleanstream-Discreet-Silicone-Shower-Enema/dp/B09641G3BR (product first available May 28, 2021).

Xplay Pro Shower Douche Black, https://www.amazon.com/Xplay-Pro-Shower-Douche-Black/dp/B0CHJCKPPZ (product first available Sep. 7, 2023).

PerfectFit Brand ergofló Impulse Compact Bulb Enema System, Removable Tip, Made from Biobased PVC and Polypropylene, Made in The USA, https://www.amazon.com/PerfectFit-ergofl%C3%B3-Removable-Biobased-Polypropylene/dp/B015L82YV8?th=1 (product first available Sep. 17, 2015).

Ergoflo Pro, https://adulttoymegastore.com/sex-toys/brands/perfect-fit/ergoflo-pro/157351/593/?srsltid=AfmBOooxGozgbctaQ10_Sdp6hV0ub5SpExg8PSKsebCO1GXx4zVkOrHZ (product available at least as of Mar. 21, 2018).

https://en.wikipedia.org/wiki/Rectal_douching (modified Mar. 10, 2024).

https://web.archive.org/web/20240711024607/https://en.wikipedia.org/wiki/Douche (cached on Jul. 11, 2024).

https://web.archive.org/web/20240708062826/https://en.wikipedia.org/wiki/Valve (cached on Jul. 8, 2024).

Fleet Enema Extra Size 7.8z 5 pk, https://www.amazon.com/Fleet-Enema-Extra-Size-7-8z/dp/B00IG0T9C6 (product first available Jul. 11, 2016).

Title 21—Food and Drugs, Chapter I—Food and Drug Administration Department of Health and Human Services. Subchapter H—Medical Devices, Part 876—Gastroenterology-Urology Device, Subpart F—Therapeutic Devices, Sec. 876.5220 Colonic irrigation system, https://www.accessdata.fda.gov/scripts/cdrh/cfdocs/cfcfr/cfrsearch.cfm?fr=876.5220#:~:text=Sec., contents%20of%20the%20lower%20colon. (last updated Sep. 27, 1996).

* cited by examiner

10

10

<u>10</u>

14

30

PORTABLE DOUCHING APPARATUS

FIELD

This invention relates in general, to body hygiene and in particular to a portable douching apparatus.

BACKGROUND

Douching refers to introducing a stream of a fluid such as water into a bodily orifice, such as vagina or rectum, and is a common practice both in the United States and abroad. Rectal douching (also referred to as anal douching) in particular is common practice in preparation for anal intercourse and can be employed for both purely hygienic and medical reasons. The removal of fecal matter from the rectum through rectal douching serves aesthetic purposes to enhance the pleasure of the sex participants and also to reduce contact with any bacteria and parasites residing in that fecal matter. Further, rectal douching can be used for delivery of microbicide, including microbicide used for pre-exposure prophylaxis of HIV, to reduce risk of disease transmission, and thus is an important public health tool.

While theoretically many kinds of tools can be used for douching, in practice, their use is limited by their portability and concealability. Due to the societal stigma commonly associated with the rectum in general and anal sex in particular, rectal douching is a highly personal act and is generally done in private. Similarly, vaginal douching is generally a highly private act. People generally do not like to advertise that they engage in the practice, especially when they are out of their home environment, and prefer devices used for the practice to be either easily concealable or not recognizable if left in open view. Thus, a useful tool for douching would be both convenient and effective for use but not easily recognizable.

While relatively simple devices exist for use in internal douching that can be hidden with relative ease, such as enema or douche bulbs and syringes, they are cumbersome, slow-to-fill (and require manual filling), and generally require multiple refills before desired cleansing can be achieved. On the other hand, conventional devices that provide nearly unlimited water supply are generally unsuitable for internal douching; for example, using a shower hose for internal douching may not provide a stream of water deep enough into the relevant orifice if left external and may actually damage tissue (thus increasing risk of disease transmission) if internal insertion is attempted.

Attempts have been made to make specialized douching tools that are connected to a shower as an unlimited water supply. However, such solutions generally require semi-permanent installation, and thus are not portable or designed for discreet use, being recognizable to someone who visits the bathroom where they are installed. For example, existing shower-powered devices, like the CleanStream™ Shower Enema System and the Aqua Shot™ Shower Enema Cleansing System by XR Brands of Huntington Beach, CA, lack portability and require installation, which limits their convenience and ability to be used discreetly. Similarly, existing examples of portable shower enema devices like the XPLAY® Pro Shower Anal Douche and Ergoflo® Pro by Perfect Fit Brand® are cumbersome and unhygienic, utilizing exposed designs with open, hanging pouches to collect and funnel shower water through the device.

Further, several U.S. patents describe a converter hose that includes a self-sealing connector connected to a hose, with the connector connecting the hose to water fixtures primarily for external applications, such as "[ . . . ] rinsing showers, animals, babies, and household items." These patents are collectively referred to as the "Lane patents" and are: U.S. Pat. No. 10,393,300 issued Aug. 27, 2019 to Lisa A. Lane; U.S. Pat. No. 11,085,567 issued Aug. 10, 2021 to Lisa A. Lane; U.S. Pat. No. 11,365,838 issued Jun. 21, 2022 to Drug Careers, Inc.; U.S. Pat. No. 11,774,021 issued Oct. 3, 2023 to Drug Careers, Inc.; and U.S. Pat. No. 11,913,577 issued Feb. 27, 2024 to Lisa A. Lane, and the entire disclosure of all of these Lane patents is incorporated by reference. However, the apparatus described in the Lane patents is not suitable for use in douching due to not accounting for the decreased flow rate that water encounters when flowing through a narrow hose recommended for rectal douching and additional resistance that water encounters upon entering an orifice for use in internal cleansing. Thus, a significant difference exists between in the flow rate at which the water enters the hose from the fixture and at which the water exists the hose. This difference in flow rates causes the water buildup in the self-sealing connector, causing the self-sealing connector to detach from the water fixture, and thus making the apparatus unusable for any extended internal use. For example, testing a converter hose without a water pressure release system showed that, when used with a 0.5 inch outside diameter (0.25 inch inside diameter) hose at medium water pressure, excess water built up, causing a ballooning effect within the elastomeric connector, resulting in its detachment from the water fixture.

Thus, there is a significant need for a portable douching apparatus that allows for quick, discreet, efficient, and safe internal cleansing.

SUMMARY

A portable douching apparatus that provides efficient and safe internal cleansing is disclosed. The douching apparatus can be used in the shower, offering a portable, discreet, and efficient, shower-powered solution for douching without the need for tools or installation. As described below, the apparatus includes a self-sealing elastomeric connector that allows a secure mounting on a shower or another water-providing fixture, a water pressure release mechanism that allows to reduce internal water pressure that could disrupt the connection to the fixture, and body-safe tip optimized for insertion into an orifice of a living organism. These features ensure a hygienic, safe internal use and compatibility with a narrow-diameter hose and tip, allowing the device to function under various levels of shower water pressure and providing a significant improvement over existing douching products.

The apparatus features a stretchy elastomeric tube, water pressure release mechanism, and a body-safe tip designed for safe internal use. The elastomeric tube stretches about the periphery of a water fixture, forming a self-sealing connection. The elastomeric tube connects to a flexible, non-metal hose via a rigid housing that includes a water pressure release system. The hose terminates in a tapered or rounded tip designed for safe internal use. The provided apparatus addresses the need for a portable, tool-free enema or douching device that can be easily attached to various water fixtures, such as shower heads, faucets or spigots.

A method of using the portable douching apparatus can include attaching the proximal end of the elastomeric connector to a fixture such as a shower head or faucet; The fixture is turned on and the water flows through the connector into other parts of the portable douching apparatus. Optionally, depending on the initial setting of the valve and the need to adjust the water pressure within the apparatus and the flow rate of the water from the tip, the water pressure is regulated by adjusting the alignment of the holes of the valve with the vents of the male portion of the housing using the notch using the opening in the housing and excess water pressure is vented through the vents. The tip is inserted into the orifice of the user, such as the anus or the vaginal opening of the user, and water exiting from the tip into the orifice is used for internal (such as rectal or vaginal) douching. Once the desired cleansing effect has been achieved, the tip is removed from the orifice, flow of the water is turned off, the elastomeric connector is detached by the user from the fixture, and the apparatus can be optionally disassembled and cleaned.

In one embodiment, a portable douching apparatus is provided. In one embodiment, the apparatus includes a flexible elastomeric connector including a first end and a second end, the first end configured to form a self-sealing connection to a fixture from which water enters the connector when the connector is connected to the fixture; a rigid housing shaped to couple to the second end of the elastomeric connector, the housing including a water pressure reduction mechanism through which some of the water that enters the housing from the connector escapes from the housing; a flexible hose one end of which is shaped to couple to the housing, wherein the water enters the flexible hose from the rigid housing through the one end when the flexible hose is coupled to the housing; and a flexible tip one end of which is shaped to receive the water from another end of the flexible hose, wherein at least an external surface of the flexible tip includes a body-safe material, at least a portion of the tip is further shaped for insertion into an orifice of a living organism, wherein at least a portion of the water flows from the flexible hose into the orifice for use in internal cleansing when the tip is inserted into the orifice, the flexible hose is coupled to the housing, the housing is coupled to the connector, and the connector is connected to the fixture.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
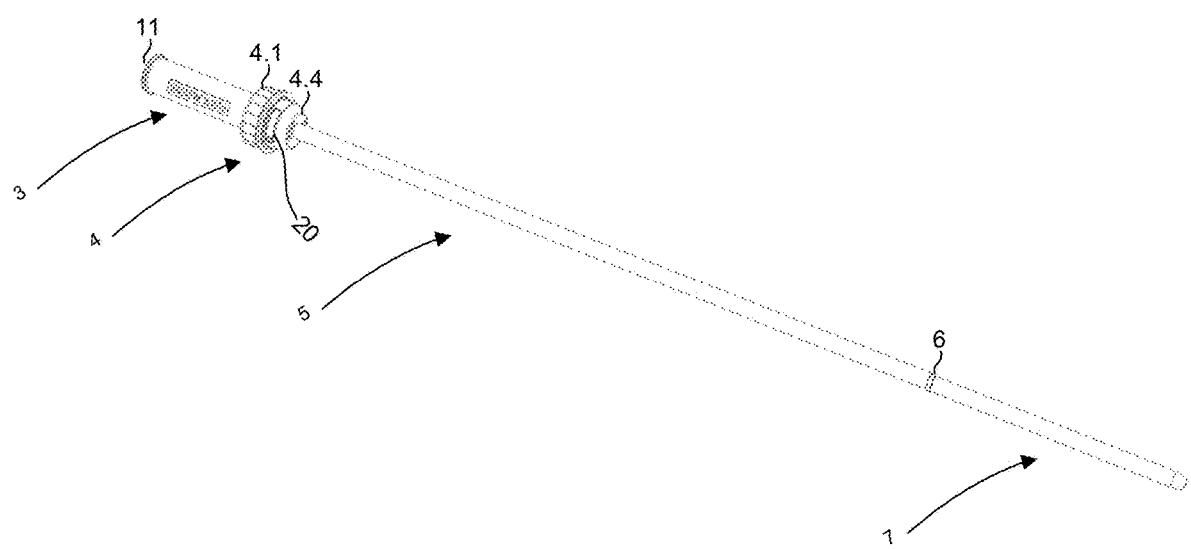
FIG. 1 is a diagram showing a perspective view of an assembled portable douching apparatus in accordance with one embodiment.

The use of the water pressure release system in the portable douching apparatus described below allows for safe use of narrow-diameter hose and tip, which are commonly recommended for douching. While in the description below, the liquid that flows through the apparatus is referred to as water, in a further embodiment, the liquid can also be water-based solutions as well as other kinds of liquids. FIG. 1 is a diagram showing a perspective view of an assembled portable douching apparatus 10 in accordance with one embodiment. The douching apparatus 10 includes a flexible elastomeric connector (3), a rigid housing (4), a flexible hose (5), a male-to-male connector (6), and a flexible tip (7). As further described below, the housing (4) includes a water pressure reduction mechanism (14) through which some of the water (2) that enters the housing from the connector escapes from the housing, including an adjustable water pressure valve (4.3) and vents for water (2) to escape. The flexible hose is a narrow-diameter hose; in one embodiment, the outside diameter of the flexible hose can be in the range from approximately 0.25 inches to 0.85 inches, though in a further embodiment, other diameters are possible. Similarly, the tip (7) can be a narrow-diameter tip with an outside diameter of in the range of 0.25-0.85 inches, though in a further embodiment, other diameters are also possible.

Figure 4:
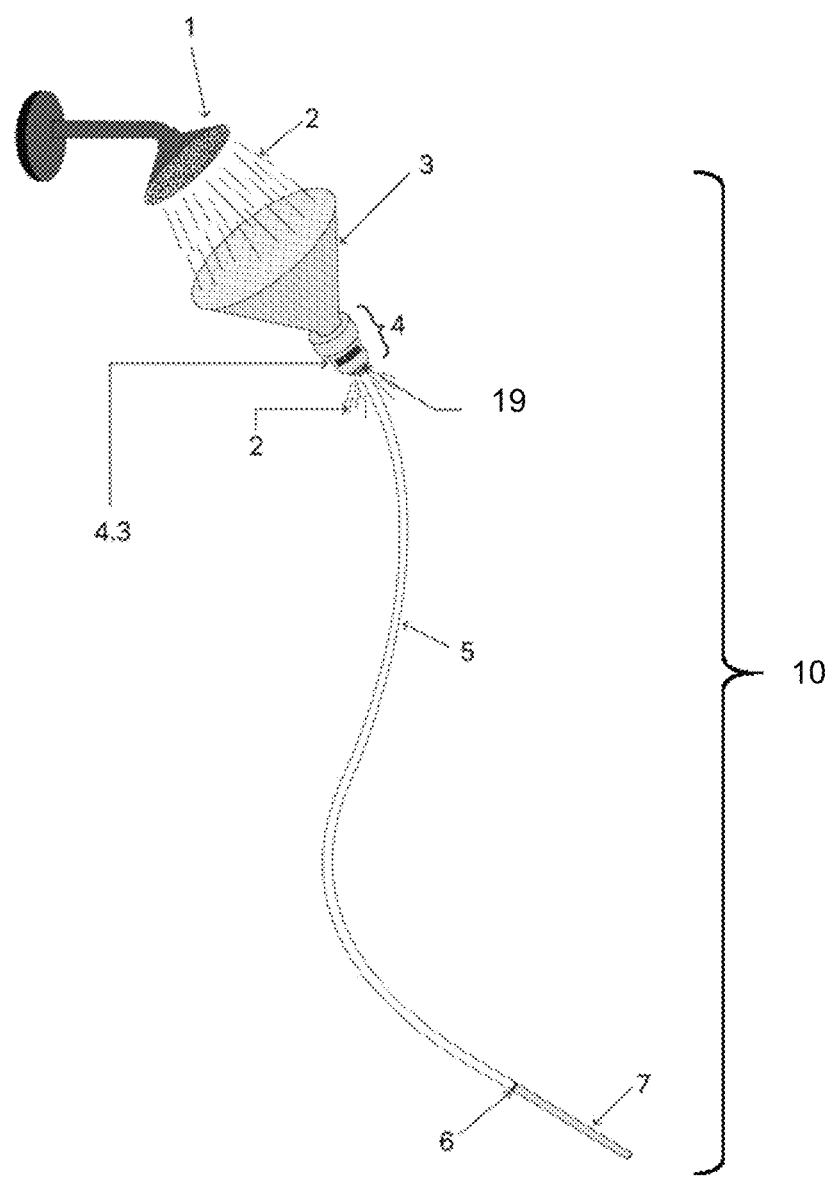
FIG. 4 is a diagram showing the portable douching apparatus of FIG. 1 attaching to a water fixture, demonstrating the flexibility of the elastomeric connector and the self-sealing connection formation.
Figure 5:
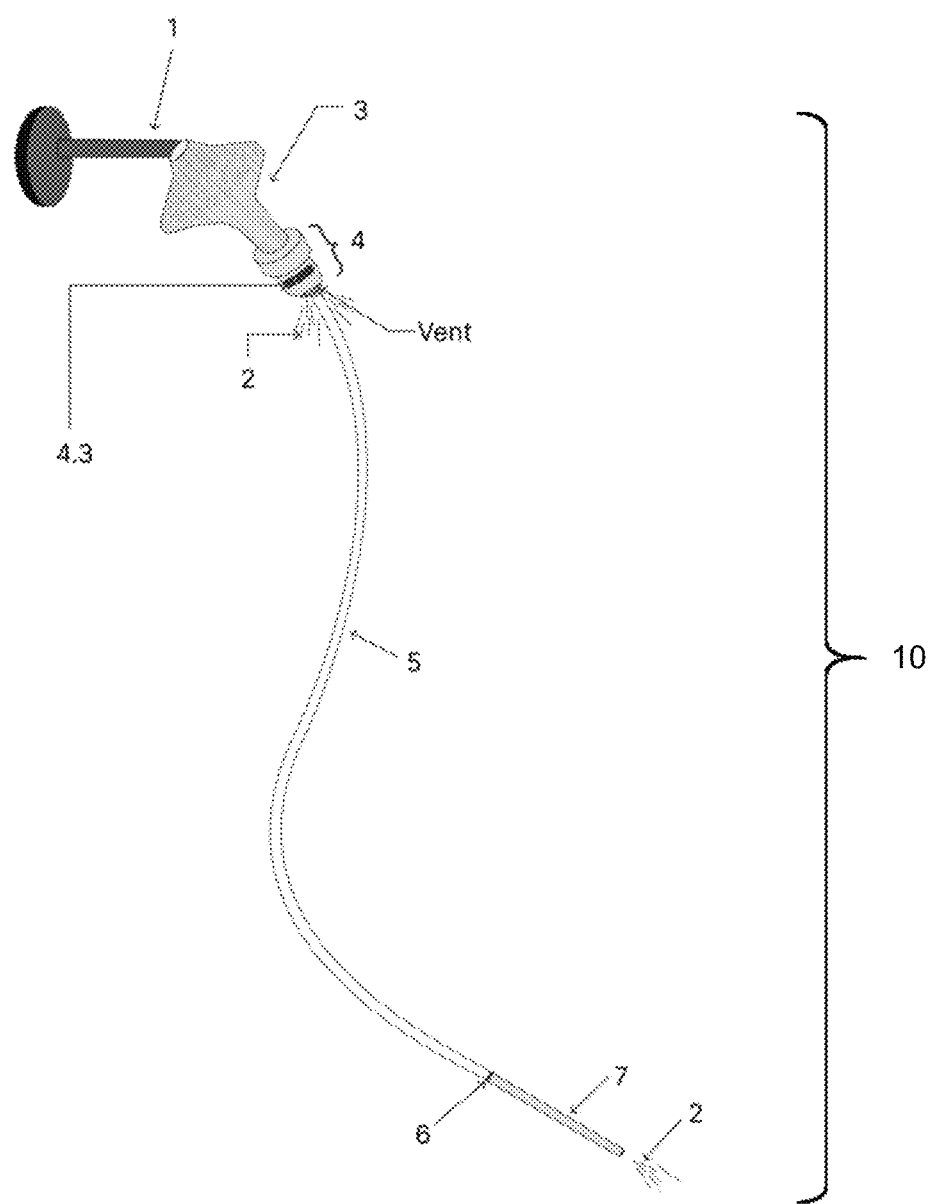
FIG. 5 is a diagram showing the portable douching apparatus of FIG. 1 in use, with the self-sealing elastomeric connector securely attached to a water fixture and with water flowing through the hose and tip and escaping from the water pressure reduction mechanism.

The flexible, hollow, elastomeric, cylindrical-shaped connector (3) has a proximal end (11) that forms a self-sealing connection to a fixture and a distal end with a perpendicular flange (15) that is shaped to couple to the rigid housing (4). The proximal end (11) of the elastomeric connector (3) can be stretched about the periphery of a fixture (1), such as a shower head, faucet, bidets, or spigot (though other fixtures (1) that can supply water are also possible), forming a self-sealing connection, as illustrated in FIGS. 4 and 5. FIG. 4 is a diagram showing the portable douching apparatus 10 of FIG. 1 attaching to a water fixture (1), demonstrating the flexibility of the elastomeric connector (3) and the self-sealing connection formation. FIG. 5 is a diagram showing the portable douching apparatus 10 of FIG. 1 in use, with the self-sealing elastomeric connector (3) securely attached to a water fixture (1) and with water (2) flowing through the hose (5) and tip (7) and escaping from the water pressure reduction mechanism (14) (shown in detail in FIG. 7). In one embodiment, the flow rate at which the water (2) enters the elastomeric connector can be 1.0-2.5 gallons per minute, though in a further embodiment, other flow rates are possible. The hose (5) is non-metal and can be made of silicone, flexible plastic, or another flexible material.

Figure 2:
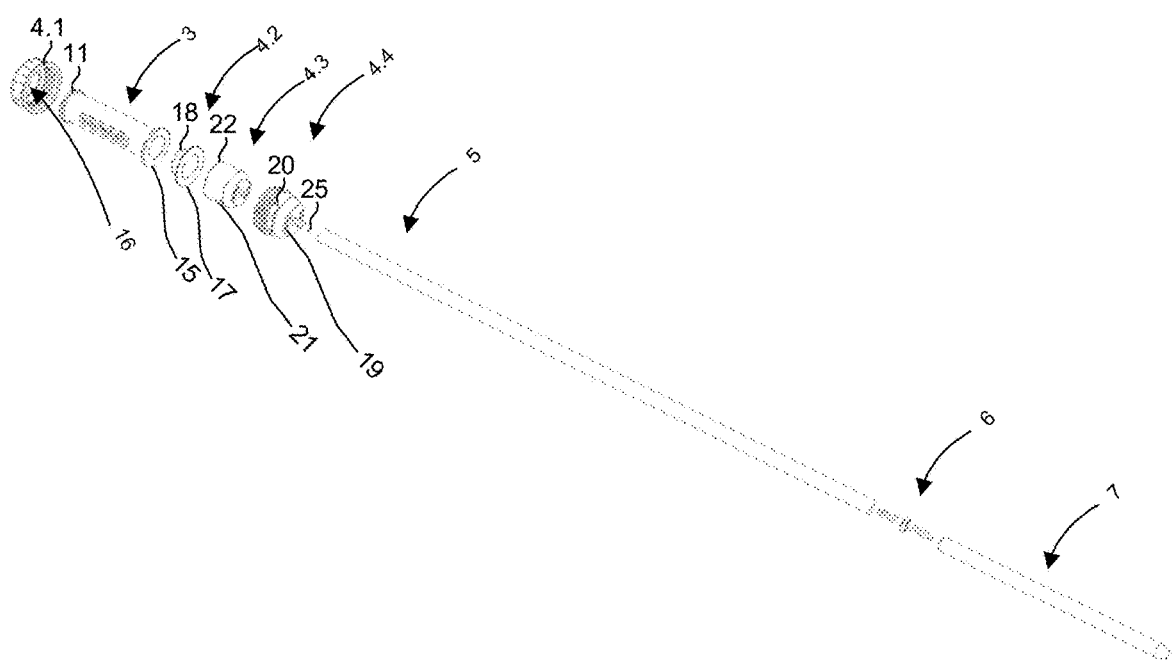
FIG. 2 is a diagram showing the portable douching apparatus of FIG. 1 disassembled in accordance with one embodiment.

FIG. 2 is a diagram showing the portable douching apparatus 10 of FIG. 1 disassembled in accordance with one embodiment. The elastomeric connector (3) comprises a thermoplastic elastomer, as described in the Lane patents cited above, the entire disclosure of which is incorporated by reference. The thermoplastic elastomer material provides adaptability and flexibility of the connector (3) to mount on different shapes and sizes of fixtures (1). In a further embodiment, other materials or combinations of materials can be used in the elastomeric connector (3) in addition to or instead of the thermoplastic elastomer. In one embodiment, the elastomeric connector (3) can be made of a thermoplastic elastomer having a durometer hardness Shore Type A or Shore Type 00 value of about 0-50 per ASTM D-2240, though in a further embodiment, other kinds of elastomers can also be used. In one embodiment, the thermoplastic elastomer of which the connector (3) is made has a tensile elongation at least in one direction at break of 50% or greater, such as in the range of 300-2000% per ASTM D-638, though in a further embodiment, other tensile elongation values are also possible. In one embodiment, thermoplastic elastomer of which the connector (3) is made has a tensile strength at least in one direction at break of 0.1-15 MPa, such as about 0.5-5 MPa per ASTM D-638, though in a further embodiment, other tensile strengths are possible. In one embodiment, the thermoplastic elastomer of which the elastomeric connector (3) is made has a tear strength of about 1-35 kN/m, such as in the range of 5-10 kN/m per ASTM D624, though in a further embodiment, other tear strengths are possible. In one embodiment, the thermoplastic elastomer of which the elastomeric connector (3) is made of has a tensile stress at least in one direction at 100% strain of less than about 15 MPa, such as in the range of 0.05-5 MPa, though in a further embodiment, other tensile strengths are possible. In one embodiment, the length of the elastomeric connector (3) can be in the range of 3 inches to 7 inches, though in a further embodiment, other lengths are also possible.

The elastomeric connector (3) includes a protruding, flanged end (15) that attaches to a housing (4) made of a rigid material such as ABS plastic (though in a further embodiment, the housing (4) can also be made of other materials). In one embodiment, the housing (4) includes a male portion (4.4) and a female portion (4.1) that are detachably coupled to each other to make up the exterior shell of the housing (4) within which another component making up the water pressure reduction mechanism 14 are located. While the male (4.4) and female (4.1) portions can be coupled together via threading located on each portion as shown in FIG. 2, other coupling ways are also possible. In a further embodiment, the exterior shell of the housing can be unitary, with the portions that are shown as male (4.4) and female (4.1) in FIG. 2 being integrally connected and not detachable from each other and thus possibly lacking female and male parts necessary for detachable coupling. While in the description below the two parts of the housing (4) making up the exterior shell are referred as male (4.4) and female (4.1), those of the described features that are not necessary for detachable coupling of the parts (4.4 and 4.1) can also be part of the unitary housing exterior shell.

The female portion (4.1) of the housing (4) is substantially cylindrically shaped and includes a circular opening (16) through which the female portion (4.1) mounts onto the elastomeric connector (3), with the flange (15) being flush against an internal surface of the female housing portion (4.1) surrounding the opening when the female housing portion (4.1) is fully mounted onto the elastomeric connector (3). In one embodiment, the flange (15) of the elastomeric connector (3) is coupled to the housing (4) by threading the proximal end of the elastomeric connector through the circular opening (16) in the female (4.1) portion of the housing (4), and compressing the flanged end (15) of the elastomeric connector against the female portion (4.1) of the housing (4) with a rigid compression insert (4.2). The rigid insert (4.2) can include a hollow tube (18) that terminates in a flat, flanged end (17). The outside diameter and length of tube portion of the insert (4.2) is less than the inside diameter and length of the elastomeric tube (3), though other dimensions of the tube portion are further possible. The outside diameter of the flat end (17) of the rigid insert (4.2) is less than the inside diameter of the female portion (4.1) of the housing (4) but greater than the diameter of the circular opening (16), though in a further embodiment, other dimensions are also possible. The tube portion (18) of the insert (4.2) is fitted into the elastomeric connector (3) while the flat, flanged end (17) of the insert (4.2) is compressed against the flanged end (15) of the elastomeric connector (3), creating a seal between the flanged end (15) of the elastomeric connector (3) and the female section (4.1) of the housing (4) when the female (4.1) and the male (4.4) halves of the housing (4) exterior are coupled together.

Figure 6:
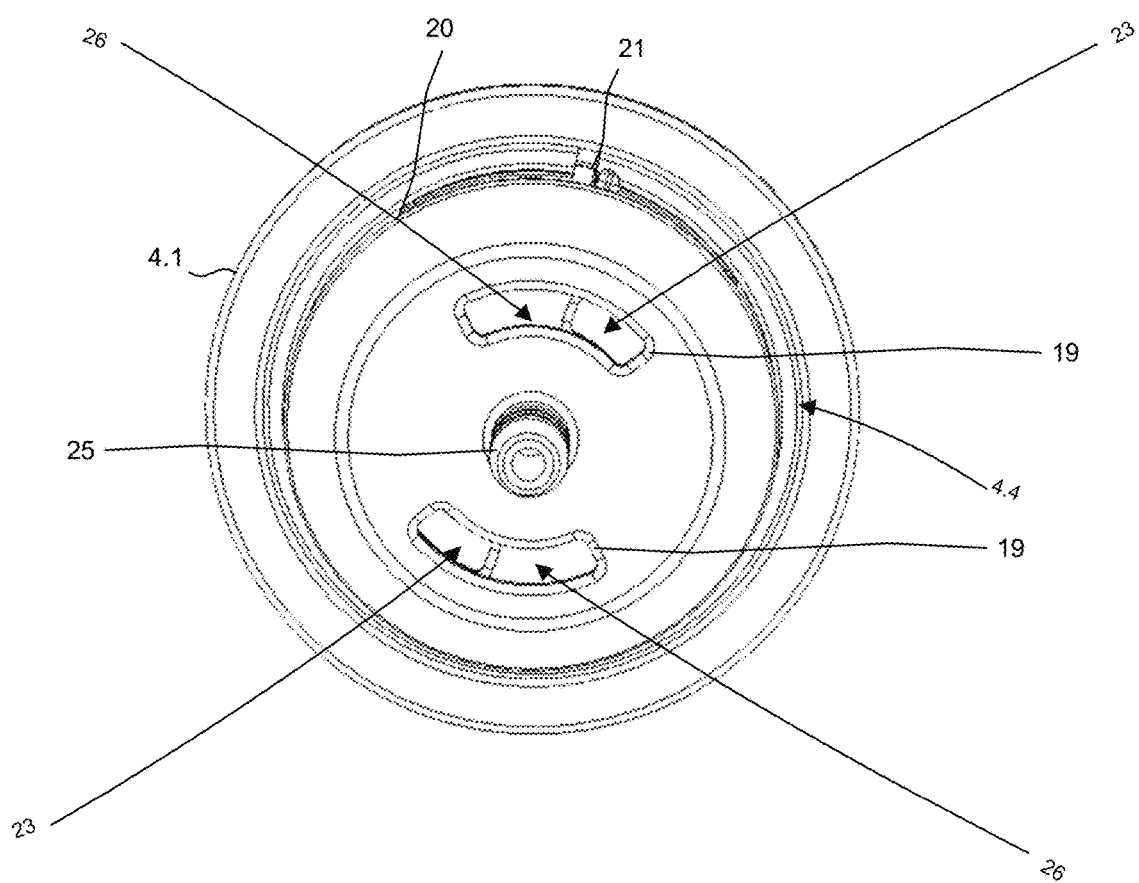
FIG. 6 is a diagram showing a front view of the housing in accordance with one embodiment.
Figure 7:
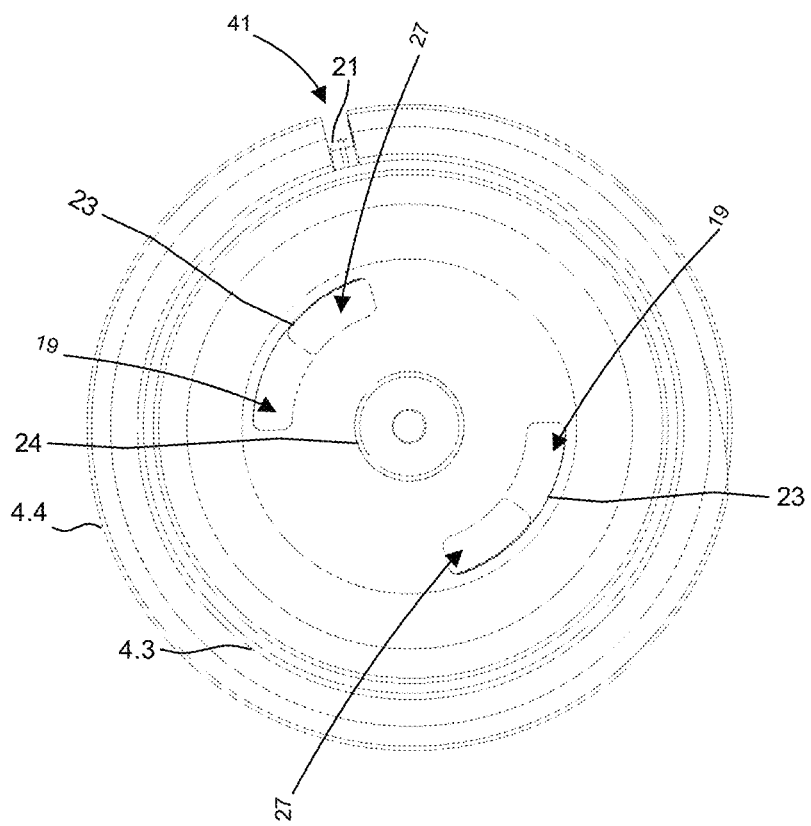
FIG. 7 is a diagram showing the water pressure reduction mechanism of the portable douching apparatus of FIG. 1, with the internal surface of the valve inserted into the male portion of the housing in accordance with one embodiment.
Figure 9:
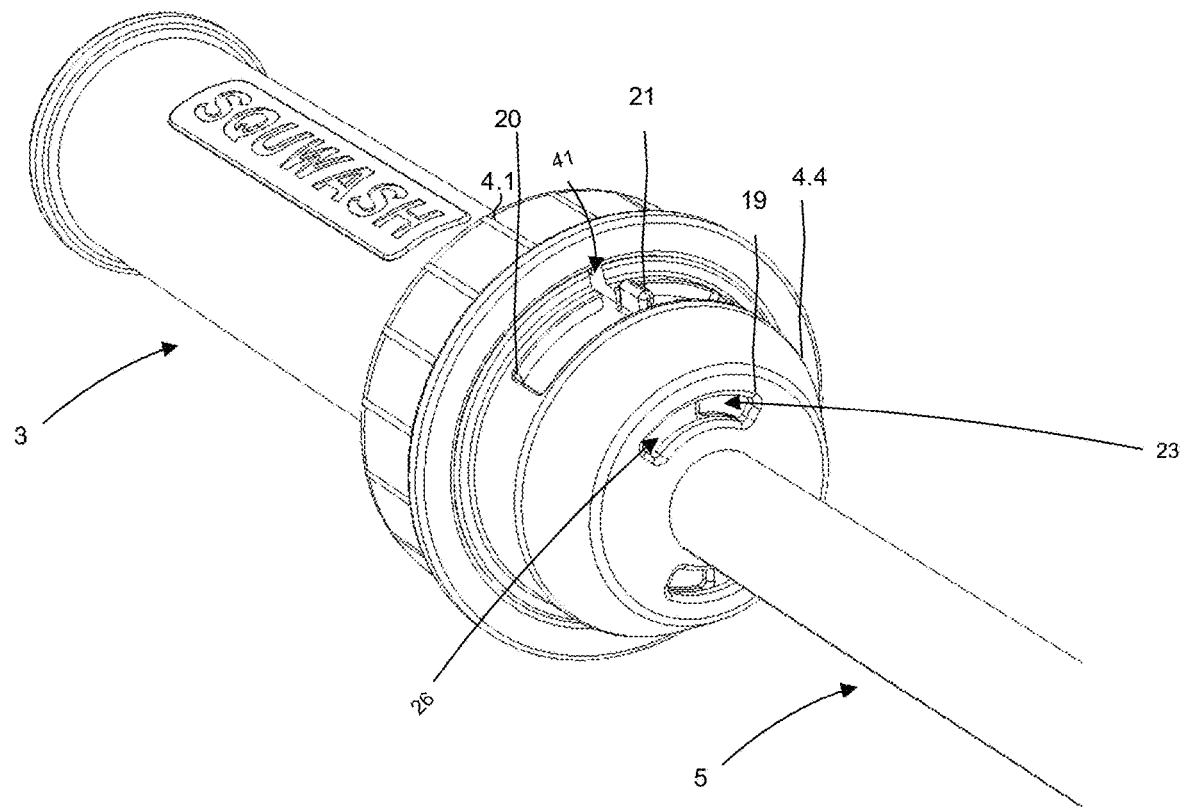
FIG. 9 is a close-up of a portion of the portable douching apparatus of FIG. 1 in accordance with one embodiment.

The water pressure reduction mechanism of the housing (4) includes the male portion (4.4) of the housing and an adjustable valve (4.3). Within the exterior shell of the housing (4) is located the adjustable valve (4.3) (also referred to as a baffle valve (4.3) due to directing the stream of the water (2)) that interfaces with the male portion (4.4) of the housing to control the proportion of the water (2) that flows into the hose (5) and the proportion of the water (2) that is released from the housing (4) (thereby reducing the water pressure within the apparatus 10). When the housing (4) is assembled, one end (22) of the valve (4.3) is pressed against the flanged end of the rigid insert (4.2) while another end of the valve (4.3) is pressed against the inner surface of the male portion (4.4) of the housing (4). The male section (4.4) of the housing includes one or more built-in vents (19) and a nozzle (25) configured for coupling to the hose (5) (with the hose (5) mounting the nozzle (25) as seen in FIG. 1), as seen in FIG. 6. FIG. 6 is a diagram showing a front view of the housing (4) in accordance with one embodiment. While FIG. 6 shows the vents (19) shown on a distal surface of the male portion (4.4) of the housing (4), the vents (19) could also be located on a different portion of the male portion (4.4). Further, while two vents (19) of a particular shape are shown in FIG. 6, other number of vents (19) and other shapes of the vents (19) are also possible. The male portion (4.4) of the housing further includes an elongated aperture (20) (also seen in FIGS. 1, 2, and 9) through which is inserted a notch 21 formed on the valve (4.3); the notch (21) can be accessed from the outside of the housing (4). The notch (21) can be inserted into the aperture (20) through a slit (41) formed in the male portion (4.4), as can be seen in FIGS. 7 and 9, though in a further embodiment, other ways to insert the notch (21) into the aperture (20) are possible. FIG. 9 is a close-up of a portion of the portable douching apparatus 10 of FIG. 1 in accordance with one embodiment.

Movement of the notch (21) within the aperture (20) rotates the valve (4.3) relative to the male portion of the housing (4.4). The valve (4.3) further includes holes (23) whose position relative to the vents (19) in the male portion (4.4) depends on the position of the notch (19) within the aperture (20). The valve (4.3) further includes an aperture (24) (shown in FIG. 7) that is always aligned with the nozzle (25) when the housing (4) is assembled. When the vents (19) and the holes (23) are entirely aligned due to the notch (21) being at one end of the aperture (20), a maximum possible amount of the water (2) escapes through the housing (4) without entering the hose (5) through the aperture (24) and the nozzle (25), thus minimizing the flow rate of the water (2) through the hose (5) relative to the flow rate from the fixture (1) and minimizing the water (2) pressure within the apparatus 10. When the notch (21) is shifted to a different position within the aperture (20), the holes (23) and the vents (19) become partially (as shown in FIGS. 6 and 7) or completely misaligned and the flow of the water (2) through the vents (19) is partially or completely blocked by the material (26) of the valve (4.3) that does not have holes and through which the water (2) cannot pass. This blockage redirects the entirety of the water (2) through the aperture (24) and the nozzle (25) into the hose (5), thus increasing (in case of partial blockage) or maximizing (in case of the complete blockage) the flow rate of the water (2) through hose (5) relative to the flow rate from the fixture (1). Thus, the use of the notch (21) allows a user to adjust both the pressure within the apparatus 10 and the flow rate of the water (2) to be used for internal cleansing. Thus, if the flow rate of the water (2) from the fixture (1) is too high, the notch (21) can be positioned to entirely align the holes (23) and the vents (19) and thus decrease the amount of water (2) retained within the apparatus (10) (and consequently keep the water (2) pressure from disrupting the connection of the connector (3) to the fixture) and the amount of water (2) that reaches the orifice being cleaned. On the other hand, if the flow rate of the water (2) from the fixture (1) is low (such as due to water shortages or other supply issues) and the entirety (or most) of the water (2) being supplied needs to be utilized, the notch (21) can be positioned to entirely (or partially) misalign the vents (19) and the holes (23), and thus increase the proportion of the water (2) provided from the fixture (1) that enters the hose (5) and reaches the orifice.

The shape of the valve (4.3) reflects the shape of the male portion (4.4) of the housing 4, with both parts of the housing (4) including a substantially cylindrical component and a substantially semi-spherical dome (though in a further embodiment, other shapes are also possible), as seen in FIG. 7. FIG. 7 is a diagram showing the water pressure reduction mechanism (14) of the portable douching apparatus 10 of FIG. 1, with the internal surface of the valve (4.3) inserted into the male portion (4.4) of the housing (10) in accordance with one embodiment. The holes (23) seen in FIG. 7 are partially aligned with the vents (19) of the male portion (4.4) and the aperture (24) is aligned with the nozzle (25) of the male portion (4.4). The portion of the holes (23) that is not aligned with the vents (19) are blocked by material (27) of the male portion (4.4) that does not have holes and that prevents passage of water (2). As seen in FIG. 7, the valve (4.3) has an outside diameter that is less than the inside diameter of the male portion (4.4) of the housing (4), fitting snugly within the male portion (4.3) of the housing (4.4). Similarly, the length of the valve (4.3) is smaller than the length of the male portion (4.4) of the housing (4.4), such that the valve (4.3) does not extend out of the male portion (4.4) of the housing (4) when the valve (4.3) is fitted in place in the assembled housing (4). In one embodiment, the size of the vents (19) and the holes (23) is a minimum of about $\frac{1}{8}^{th}$ of an inch×$\frac{1}{8}^{th}$ of an inch (such as $\frac{1}{8}^{th}$ of an inch×$\frac{5}{8}^{th}$ of an inch), though in a further embodiment, other dimensions of both the vents (19) and the holes (23) (including dimensions that are not identical between the holes (23) and the vents (19)) are possible. While particular shapes of the vents (19) and the holes (23) are shown in FIGS. 6 and 7, other shapes of the vents (19) and holes (23) are possible. Further, while particular numbers of the holes (23) and vents (19) are seen with reference to FIGS. 6 and 7, other numbers of the holes (23) and vents (19) are also possible.

Returning to FIG. 2, the nozzle (25) of the male portion (4.4) includes ridges that create a secure attachment between the housing (4) and the hose (5) without the need for clamps. The hose (5) mounts onto the nozzle (25) with one end and connects to a tip (7) on the opposite end. In the embodiment shown in FIG. 2, the connection between the tip (7) and the hose (5) is accomplished using a rigid male-to-male connector (6) through which the water (2) flows from the hose (5) into the tip (7). In one embodiment, the male-to-male connector (6) can be made of ABS plastic, though in a further embodiment, other materials or combinations of materials are also possible. In a further embodiment, the tip (7) can be integrally attached to the end of the hose (5) opposite to the end that attaches to the housing (4).

The tip (7) provides a conduit through which water (2) from the hose (5) enters the orifice, being insertable into the orifice such as the anus or vagina. Due to making contact with delicate tissue, at least the exterior of the tip (7) that makes contact with the tissue is made of a body safe material, such as FDA-approved body-safe silicone (though other body safe materials are also possible), and features a rounded or tapered end to allow for comfortable insertion into the body, ensuring the apparatus 10 is suitable for internal use. The material of the tip (7) (or at least the exterior of the tip (7)) can further have antiseptic properties to further increase the safety of the use of the apparatus 10. The antiseptic properties can be accomplished by curing the material of which the tip (or at least the exterior of the tip (7)) is made with another material that has antiseptic properties. Thus, the tip (7) (or at least the exterior of the tip (7)) can be made of platinum-cured silicone (such as ISO 10993 biocompatible platinum-cured silicone) or silicone cured with silver ions, though other additional materials with antiseptic properties are also possible.

Figure 3:
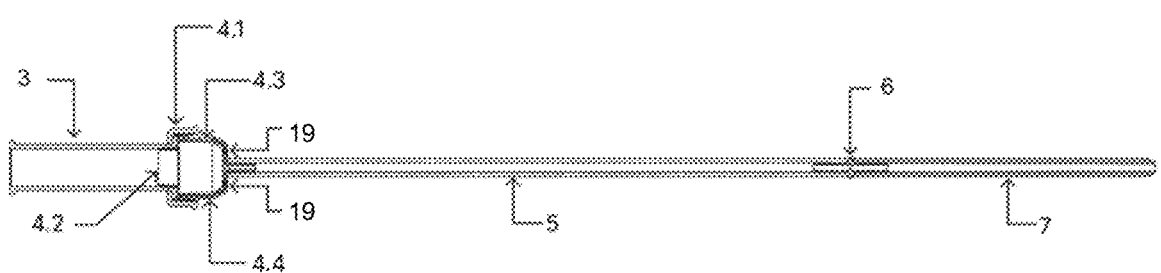
FIG. 3 is a cross-sectional view of the portable douching apparatus of FIG. 1 in accordance with one embodiment.

Until a certain threshold, the flow rate of the water (2) through the apparatus 10 is proportional to the flow rate at which the water (2) comes out from the fixture (1), with the water (2) pressure reduction mechanism of the housing (4) allowing to modify that flow rate under the control of the user and release excess water (2) pressure, as illustrated by FIG. 3. FIG. 3 is a cross-sectional view of the portable douching apparatus 10 of FIG. 1 in accordance with one embodiment. Water (2) flows through the elastomeric connector (3), the housing (4.2, 4.3, 4.4), hose (5), and tip (7). From the tip (7), the water (2) can enter the orifice that is being in internally cleansed.

Figure 8:
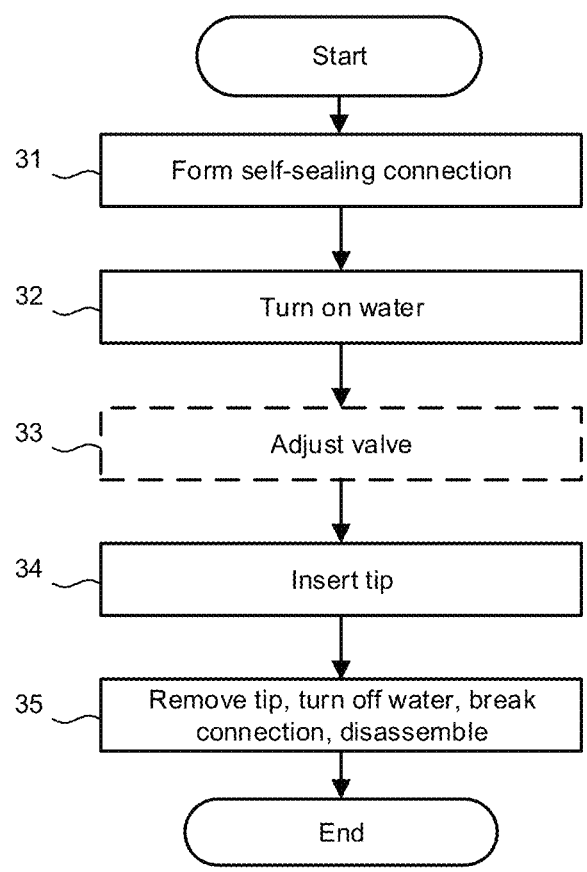
FIG. 8 is a diagram showing a method of use of the portable douching apparatus of FIG. 1 in accordance with one embodiment.

The use of the apparatus (10) allows to privately and conveniently perform douching in any location that provides a steady flow of water (2), thus providing for true portability of the apparatus. FIG. 8 is a diagram showing a method (30) of use of the portable douching apparatus (10) of FIG. 1 in accordance with one embodiment. Initially, the proximal end of the elastomeric connector (3) is stretched about the periphery of a fixture (1), such as a shower head or faucet, forming a self-sealing connection, as illustrated in FIG. 5 (step 31). Once the elastomeric connector (3) is securely attached to the fixture, water (2) in the fixture (1) is turned on and flows into the apparatus 10 (step 32). Optionally, depending on the initial setting of the valve (4.3) and the need to adjust the water (2) pressure within the apparatus and the flow rate of the water (2) from the tip (7), the water (2) pressure is regulated by adjusting the alignment of the holes (23) of the valve (4.3) with the vents (19) using the notch (21) using the opening (20) in the housing (4) and excess water (2) pressure is vented through the vents (19) (step 33). The tip (7) is inserted into the orifice of the user, such as the anus or the vaginal opening of the user, and water (2) exiting from the tip (7) into the orifice is used for internal (rectal or vaginal) douching (step 34). Once the desired level of cleansing has been achieved, the tip (7) is removed from the orifice, flow of the water (2) is turned off, the elastomeric connector (3) is detached by the user from the fixture (1), and the apparatus (10) can be optionally disassembled and cleaned (step 35), ending the method (30). In one embodiment, the insertion and removal of the tip (7) can be performed multiple times before the apparatus 10 is disassembled, with additional water being added from the tip (7) into the living organism after each insertion, though in a further embodiment, only a single insertion and removal can be done.

USE EXAMPLES

The following examples are given for illustrative purposes and for purposes of limitation.

Example 1: Using the Device with a Shower Head

To use the douching apparatus 10 with a shower head, the proximal end of the elastomeric connector (3) is stretched about the periphery of the shower head (1) to form a secure, self-sealing connection. Once the connection is established, water (2) flows through the elastomeric connector (3). Water (2) pressure is regulated by adjusting the position of the valve (4.3), and excess pressure is vented through the vents (19) of the housing (4). Water (2) flows through the hose (5) and exits via the body-safe tip (7), which is specifically designed for safe and comfortable internal use.

The advantages of the use of the water pressure release mechanism of the apparatus 10 are seen from the following data. The apparatus 10 and a partial apparatus ("partial apparatus") in which the elastomeric connector (3) was directly attached to the hose (5) that was attached to the tip (7) but did not include the housing (4) were tested by attaching them (one at a time) to a shower head providing water (2) at 1.5 gallons per minute (GPM). The hose (5) used both in the apparatus (10) and the partial apparatus had an inside diameter of 0.25 inches and an outside diameter of 0.5 inches. Once the water (2) flow started, water (2) immediately began to accumulate in the elastomeric connector of the partial apparatus due to the narrow diameter of the hose, the 1.5 GPM flow rate from fixture, and the absence of any water pressure release mechanism. Water (2) flowed through the connector (3) and hose (5) of the partial apparatus, exiting from the tip at a rate of 0.57 GPM. The connector (3) quickly detached from the shower head after approximately 26 seconds due to excessive water (2) accumulating in the elastomeric connector. On the contrary, no ballooning occurred when the apparatus 10 was used when water (2) was allowed to escape through at least two vents each sized approximately at $\frac{1}{8}^{th}$ inch×$\frac{1}{8}^{th}$ inch. Water (2) that did not escape through the vents flowed through the hose and tip at a rate of 0.5 GPM. When the notch (21) is turned to maximize the flow of water (2) through the vents (19) (i.e. valve holes (23) and male portion (4.4) vents (19) are fully aligned), water (2) escaped from the tip at a rate of 0.411 GPM.

Example 2: Using the Device with a Faucet

The douching apparatus 10 can also be connected to a faucet. The proximal end of the elastomeric connector (3) is stretched about the periphery of the faucet, forming a self-sealing connection similar to the connector's (3) use with a shower head. For narrow diameter fixtures, such as faucets, the proximal end of the elastomeric connector may be rolled up onto itself to ensure a tighter, leak-proof connection. As water flows through the device, the water pressure release system (4.3) effectively vents excess pressure through built-in vents (19) in the housing (4.4). Water (2) flows through the hose (5) and exits via the detachable, body-safe tip (7), ensuring a safe and efficient internal cleansing process.

While the apparatus 10 is described above as being suitable for internal cleansing of the rectum (through insertion of the tip (7) into the anus) or the vagina (through insertion of the tip (7) into the vaginal opening), in a further embodiment, the apparatus could be used for internal cleansing of other parts of a living organism, including for cleansing of parts of the gastrointestinal tract other than the rectum. Further, while in the description above, the living organism on which the apparatus 10 is used is described as a human, in a further embodiment, the apparatus 10 could also be used for internal cleansing of an animal. In addition, while the internal cleansing for which the apparatus 10 is described above is referred to as douching, depending on the amount of time water is supplied through the tip (7) and the depth of insertion of the tip (7), deeper levels of cleansing are possible, allowing the use of the apparatus (10) as an enema.

While the word "Squwash" appears on the elastomeric connector (3) in some of the FIGURES, the word has no functional significance and the elastomeric connector (3) can be made without the word or with another word on the connector's surface.

While the invention has been particularly shown and described as referenced to the embodiments thereof, those skilled in the art will understand that the foregoing and other changes in form and detail may be made therein without departing from the spirit and scope of the invention.

What is claimed is:

1. A portable douching apparatus comprising:
   a flexible elastomeric connector comprising a first end and a second end, the first end configured to form a self-sealing connection to a fixture from which water enters the flexible elastomeric connector when the flexible elastomeric connector is connected to the fixture, the flexible elastomeric connector further comprising a flange formed on the second end of the flexible elastomeric connector;
   a rigid housing shaped to couple to the second end of the flexible elastomeric connector, the rigid housing further comprising:
      a first housing portion comprising an opening through which the first housing portion mounts onto the flexible elastomeric connector, wherein the flange is flush against an internal surface of the first housing portion surrounding the opening when the first housing portion is fully mounted onto the flexible elastomeric connector;
      a rigid insert comprising a hollow extended portion insertable into the second end of the flexible elastomeric connector and a flanged portion that is pressed against the flange of the flexible elastomeric connector when the rigid insert is inserted into the flexible elastomeric connector;
      an adjustable valve that regulates flow of the water through the rigid housing and that comprises one or more holes;
      a notch formed on an outside surface of the adjustable valve;
      a second housing portion comprising one or more vents through which some of the water that passes through the adjustable valve is released from the rigid housing and forming an exterior of the rigid housing together with the first housing portion, wherein a first portion of the adjustable valve is shaped to press against a part of the flanged portion of the rigid insert and a second portion of the adjustable valve is shaped to press against an inner surface of the second housing portion when the adjustable valve is positioned within the rigid housing; and an elongated aperture formed within the second housing portion, wherein the notch is inserted into the elongated aperture when the adjustable valve is positioned within the rigid housing, wherein the notch is movable within the elongated aperture, wherein the movement of the notch within the elongated aperture rotates the adjustable valve, wherein the rotation of the adjustable valve controls alignment of the one or more holes with the one or more vents, and wherein the alignment controls an amount of the water released through the one or more vents;

a flexible hose having a first end which is shaped to couple to the rigid housing, wherein at least a portion of the water that passes through the adjustable valve and that is not released through the one or more vents enters the flexible hose from the rigid housing through the first end of the flexible hose when the flexible hose is coupled to the rigid housing; and a flexible tip having a first end which is shaped to receive at least the portion of the water from a second end of the flexible hose, wherein at least an external surface of the flexible tip comprises a body-safe material, at least a portion of the flexible tip is further shaped for insertion into an orifice of a living organism, wherein at least the portion of the water flows from the flexible hose through the flexible tip into the orifice for use in internal cleansing when the flexible tip is inserted into the orifice, the flexible hose is coupled to the rigid housing, the rigid housing is coupled to the flexible elastomeric connector, the flexible elastomeric connector is connected to the fixture, and the water is flowing from the fixture.

2. The douching apparatus according to claim 1, wherein an outside diameter of the flexible hose is between 0.25 inches and 0.85 inches, and wherein the second end of the flexible hose is detachably couplable to the flexible tip.

3. The douching apparatus according to claim 1, wherein the amount of the water released through the one or more vents is inversely proportional to a flow rate of at least the portion of the water through the flexible tip.

4. The douching apparatus according to claim 1, further comprising a nozzle formed on the second housing portion and shaped to insert into the first end of the flexible hose, wherein at least the portion of the water that passes through the adjustable valve and that is not released through the one or more vents enters the flexible hose through the nozzle.

5. The douching apparatus according to claim 4, wherein the nozzle comprises a plurality of notches that promote secure attachment of the nozzle to the flexible hose.

6. The douching apparatus according to claim 1, wherein one of:
the first housing portion and the second housing portion are integral components of the exterior of the rigid housing and together form the exterior of the rigid housing; and
one of the first housing portion or the second housing portion is female and another of the first housing portion or the second housing portion is male and the first housing portion and the second housing portion removably couple to each other.

7. The douching apparatus according to claim 1, further comprising a male-to-male insert configured to couple to the second end of the flexible hose and to the first end of the flexible tip, wherein at least the portion of the water flows from the flexible hose into the flexible tip through the male-to-male insert.

8. The douching apparatus according to claim 1, wherein the flexible tip is one of tapered or rounded.

9. The douching apparatus according to claim 1, wherein the body-safe material comprises silicone.

10. The douching apparatus according to claim 9, wherein the external surface of the flexible tip further comprises a material with antiseptic properties.

11. The douching apparatus according to claim 10, wherein the material with antiseptic properties comprises silver ions.

12. The douching apparatus according to claim 10, wherein the silicone is platinum-cured silicone.

13. The douching apparatus according to claim 1, wherein a flow rate of the water from the fixture is 1 to 2.5 gallons per minute.

14. The douching apparatus according to claim 1, wherein the fixture is one of a shower head or a faucet.

15. The douching apparatus according to claim 1, wherein an escape of the water through the one or more vents promotes the self-sealing connection from being disrupted by pressure of the water within the flexible elastomeric connector.

16. The douching apparatus according to claim 1, wherein one of:
the flexible tip is integrally connected to the flexible hose; or
the flexible tip is removably coupled to the flexible hose.

* * * * *